United States Patent [19]

Dietsche et al.

[11] Patent Number: 4,753,885

[45] Date of Patent: Jun. 28, 1988

[54] FOAM CONTROL IN THE SUGAR INDUSTRY AND IN THE YEAST INDUSTRY

[75] Inventors: Wolfram Dietsche, Frankenthal; Klaus Lorenz, Worms; Christos Vamvakaris, Kallstadt; Albert Hettche, Hessheim, all of Fed. Rep. of Germany

[73] Assignee: BASF Aktiengesellschaft, Ludwigshafen, Fed. Rep. of Germany

[21] Appl. No.: 77,091

[22] Filed: Jul. 23, 1987

Related U.S. Application Data

[63] Continuation of Ser. No. 788,573, Oct. 17, 1985, abandoned.

[30] Foreign Application Priority Data

Oct. 19, 1984 [DE] Fed. Rep. of Germany ....... 3438389

[51] Int. Cl.⁴ .......................... C12N 1/00; C12N 1/16; C12N 1/18
[52] U.S. Cl. .................................... 435/243; 435/255; 435/256; 435/267; 435/274; 435/276; 435/812
[58] Field of Search ............... 435/812, 274, 276, 267, 435/243, 255, 256; 585/7; 252/307, 351, 358

[56] References Cited

FOREIGN PATENT DOCUMENTS

| | | |
|---|---|---|
| 0706357 | 3/1965 | Canada . |
| 2164907 | 7/1973 | Fed. Rep. of Germany . |
| 1337677 | 4/1963 | France . |
| 775483 | 5/1957 | United Kingdom . |
| 1371731 | 10/1974 | United Kingdom . |

OTHER PUBLICATIONS

Kirk–Othmer, *Encyclopedia of Chemical Technology*, 3rd edition, vol. 7, (1979), pp. 430–447.

*Primary Examiner*—Charles F. Warren
*Assistant Examiner*—Elizabeth A. Hanley
*Attorney, Agent, or Firm*—Oblon, Fisher, Spivak, McClelland & Maier

[57] ABSTRACT

Foam is controlled in the sugar industry and yeast industry by a process in which oxyalkylation products of the formula I

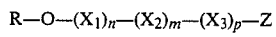

$$R-O-(X_1)_n-(X_2)_m-(X_3)_p-Z$$

where R is alkyl of 6 to 22 carbon atoms or alkylphenyl where alkyl is of 6 to 12 carbon atoms, $X_1$ and $X_3$ are ethylene oxide units, n and p are each from 0 to 15 and the sum of n and p is not less than 2, the groups $X_2$ are propylene oxide and/or butylene oxide units, m is from 0 to 15 and Z is straight-chain or branched alkyl of 1 to 4 carbon atoms, allyl or benzyl, having a turbidity point of <75° C., are used as antifoams.

7 Claims, No Drawings

FOAM CONTROL IN THE SUGAR INDUSTRY AND IN THE YEAST INDUSTRY

This application is a continuation of application Ser. No. 788,573, filed on Oct. 17, 1985, now abandoned.

The present invention relates to a process for controlling foam in the sugar industry and in the yeast industry using fatty alcohol or alkylphenol oxyalkylates possessing blocked terminal groups.

In the industrial processing of sugar-containing plant juices, as carried out on a large scale in the recovery of sugar from sugar beet and from sugar cane, as well as in the production of baker's yeast using molasses, it is necessary to add suitable assistants to reduce foam formation to an acceptable level or to prevent it completely.

The formation of stable foams is due to certain surfactant substances, such as humic acids, protein substances, degradation products of protein and starch, pectins and saponins, as occur very widely in nature. Hence, the amount of foam formers varies depending on the year of harvesting and the region of cultivation.

The formation of undesirable foams can greatly hinder production in sugar and yeast factories, for example because the capacity of the plant cannot be fully utilized, or foam formation may result in substantial losses of crude juice or of yeast.

In a sugar factory, an excessive build-up of foam can give rise to particular difficulties in the diffusors, in the clarification apparatuses, in the carbonization tanks and in the evaporators. Although a certain amount of foam should be formed in the fermentation vats in a yeast factory in order to ensure better aeration, it should not exceed a certain level. The substances used for controlling foam must be removed substantially in the conventional working up of the end product, for example during refinement of the sugar or during washing of the yeast, so that they can no longer be detected in the final product. Moreover, all assistants used in the preparation of foodstuffs should be odorless and tasteless and of course completely physiologically acceptable.

For economic reasons, and in order that the amount of foreign substances due to the addition of antifoams is kept as small as possible in the sugar-containing substrates, particularly efficient antifoams are desirable. In the production of yeast, moreover, the antifoam must not have an adverse effect on the growth of the yeast cells and hence on the yield of yeast.

When antifoams are used in practice, it is also important that they have a long-lasting effect. Some antifoams which are initially highly effective become ineffective after a short time, presumably because the substances which are initially sparingly soluble gradually become finely dispersed in the substrate in which foam is to be suppressed. Accordingly, further amounts of antifoam have to be added constantly in such a case, so that assistants of this type are uneconomical.

In the sugar industry and yeast industry, oily fats, such as colza oil, peanut oil and olive oil, and wool fat and mineral oil have long been used for inhibiting foam. Fatty acid monoglycerides, fatty acid polyglycol esters, polyalkylene glycols, esters of talloleic acids, and adducts of ethylene oxide with alkylphosphoric acids and with branched fatty alcohols have also been suggested for this purpose. Although foam can generally be suppressed to a greater or lesser extent by means of these substances, they are not completely satisfactory for a variety of reasons, in particular because of the excessively large amounts required. The high consumption is attributable in some cases to an action which is not sufficiently long-lasting.

German Published Application DAS No. 2,164,907 describes special antifoams for the sugar industry and yeast industry. The fatty alcohol/alkylene oxide adducts described there constitute an improvement over the prior art without completely meeting the requirements set, ie. a good action coupled with very low consumption. To improve performance, it is often necessary to resort to combinations with conventional antifoams.

It is an object of the present invention to provide antifoams for the sugar industry and yeast industry which are completely toxicologically and physiologically acceptable and have a maximum foam-inhibiting effect when used in very small amounts.

We have found, surprisingly, that this object is achieved if adducts of alkylene oxides with straight-chain or branched, saturated aliphatic alcohols of 6 to 22 carbon atoms or alkylphenols where alkyl is of 6 to 12 carbon atoms, whose terminal groups are blocked by etherification, are employed as antifoams in the sugar industry and yeast industry.

The present invention relates to a process for controlling foam in the sugar industry and yeast industry, wherein a fatty alcohol oxyalkylate or alkylphenol oxyalkylate of the formula I

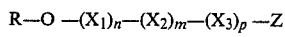

$$R-O-(X_1)_n-(X_2)_m-(X_3)_p-Z$$

which possesses a blocked terminal group and in which R is alkyl of 6 to 22 carbon atoms or alkylphenyl where alkyl is of 6 to 12 carbon atoms, $X_1$ and $X_3$ are each ethylene oxide units, n and p are each 0 to 15 and the sum of n and p is not less than 2, the groups $X_2$ are propylene oxide and/or butylene oxide units, m is 0 to 15 and Z is a straight-chain or branched alkyl radical of 1 to 4 carbon atoms, allyl or benzyl, and which has a turbidity point of <75° C., is used as an antifoam.

Surprisingly, foam inhibition is significantly improved compared with the prior art when the special compounds of the formula I are used, although a skilled worker in the surfactant sector is familiar with the fact that it is in general impossible to achieve any additional foam inhibition by means of, for example, a terminal group blocked with methyl. Particularly noteworthy in comparison with the most recent prior art (German Published Application DAS No. 2,164,907) is the substantial improvement in efficiency, which is achieved by blocking the terminal group. In some cases, the same effect can be achieved with the novel antifoams as with twice the amount of antifoams not possessing blocked groups and containing OH groups.

Alkyl radicals Z, in addition to methyl and ethyl, are, for example, n-propyl, isopropyl, n-butyl, sec.-butyl and isobutyl.

Preferred oxyalkylation products possessing blocked terminal groups are those based on C 8-C 18-fatty alcohols and from 2 to 10 ethylene oxide units and from 2 to 12 propylene oxide units, where the ratio of ethylene oxide to propylene oxide is from 3:1 to 1:3 and Z is methyl, ethyl or allyl. R is very particularly preferably straight-chain or branched alkyl of 9 to 15 carbon atoms.

The turbidity point is the temperature above which the oxyalkylate used is present as a mixture of two liquid phases, in a 1:3 mixture of the butylene diglycol and water (cf. DIN 53,917).

In conformity with the definition, starting materials for the preparation of the surfactants used according to the invention are fatty alcohols or mixtures of fatty alcohols of 6 to 22 carbon atoms. They may be branched or linear and in the form of their isomer mixtures or their mixtures as obtained in the preparation.

Examples of these are octanol, nonanol, decanol, dodecanol, tetradecanol, hexadecanol, octadecanol (stearyl alcohol) as well as mixtures of these.

Those obtained by the Ziegler synthesis and in particular by the oxosynthesis are particularly preferred industrially. Individual cuts of $C_{10}$- or $C_{13}$-alcohols or $C_9/C_{11}$, $C_{13}/C_{15}$ or $C_{16}/C_{18}$ alcohol mixtures, prepared by the oxosynthesis, are preferred. The $C_{10}/C_{12}$, $C_{10}/C_{14}$ and $C_{12}/C_{16}$ alcohol mixtures obtained by the Ziegler synthesis are just as advantageous. The $C_{13}/C_{15}$ cut of the alcohol fraction obtained by the oxosynthesis is particularly advantageous. The $C_{12}/C_{14}$-coconut fatty alkyl radical and $C_{16}/C_{18}$ tallow fatty alkyl radical are also particularly noteworthy.

Examples of alkylphenols which are suitable starting materials are hexylphenol, octylphenol, nonylphenol, decylphenol and dodecylphenol.

Some of the oxyalkylates used according to the invention are known; those which are unknown are prepared in a conventional manner by oxyalkylation. The resulting oxyalkylates are then converted to the corresponding ethers using an alkylating agent. Thus, the preparation of the antifoams used according to the invention is known from the literature and does not require a general description.

The specific preparation of some selected compounds is described in the Examples.

The Examples which follow illustrate the invention without restricting it.

Preparation Examples

EXAMPLE 1

20.8 parts of a $C_{13}/C_{15}$ alcohol mixture obtained by the oxosynthesis and 0.1 part of potassium hydroxide were initially taken in an autoclave, and 26.4 parts of ethylene oxide gas were introduced continuously at from 110° to 120° C. To complete the reaction, stirring was continued for one hour. 23.2 parts of propylene oxide were then added continuously at from 130° to 140° C., and the mixture was left to continue reacting for 2 hours. 19 parts of the resulting fatty alcohol oxyalkylate were mixed with an equimolecular amount of KOH at room temperature and converted to the alcoholate. The product was then etherified with 4.45 parts of dimethyl sulfate. The inorganic products were separated off from the end product by extraction with water. This process was repeated several times until the OH number of the end product was <8. The residual water was removed by distillation under reduced pressure, and salt residues were removed by filtration.

17 parts of an antifoam possessing blocked terminal groups and having an OH number of 7 were obtained. The residual water, determined by the Karl Fischer method, was about 0.3%. The turbidity point of a 2% strength solution in 1:3 butylene diglycol/water was 68/69° C.

The antifoams used according to the invention and shown in Table 1 below are prepared in a similar manner. Depending on the meaning of Z, the reaction was carried out using dimethyl sulfate, diethyl sulfate, allyl chloride or benzyl chloride as the alkylating agent. Blocking of the terminal groups corresponds to a residual OH number of <15, preferably <10. The OH number is therefore a measure of the completeness of the etherification reaction.

TABLE 1

| Example | R | $(X_1)_n$ | $(X_2)_m$ | $(X_3)_p$ | Z | Turbidity point, °C. (2% strength in 1:3 BDG*/water) |
|---|---|---|---|---|---|---|
| 1 | $C_{13}$-$C_{15}$—alkyl (oxo) | $(C_2H_4O)_6$ | $(C_3H_6O)_4$ | — | $CH_3$ | 68–69 |
| 2 | $C_{13}$-$C_{15}$—alkyl (oxo) | $(C_2H_4O)_5$ | $(C_3H_6O)_4$ | — | $CH_3$ | 64 |
| 3 | $C_{13}$-$C_{15}$—alkyl (oxo) | $(C_2H_4O)_5$ | $(C_3H_6O)_3$ | — | $CH_3$ | 66 |
| 4 | $C_{13}$-$C_{15}$—alkyl (oxo) | — | $(C_3H_6O)_4$ | $(C_2H_4O)_2$ | $CH_3$ | 70–71 |
| 5 | $C_{13}$-$C_{15}$—alkyl (oxo) | $(C_2H_4O)_6$ | $(C_3H_6O)_4$ | — | Allyl | 64–65 |
| 6 | $C_{16}$-$C_{18}$—alkyl | $(C_2H_4O)_8$ | $(C_3H_6O)_4$ | — | $CH_3$ | 64 |
| 7 | $C_{10}$-$C_{12}$—alkyl (Ziegler) | $(C_2H_4O)_5$ | $(C_3H_6O)_3$ | — | $CH_3$ | 70–71 |
| 8 | $C_{10}$-$C_{12}$—alkyl (Ziegler) | $(C_2H_4O)_5$ | $(C_3H_6O)_3$ | — | $C_2H_5$ | 68 |
| 9 | $C_{10}$-$C_{12}$—alkyl (Ziegler) | $(C_2H_4O)_5$ | $(C_3H_6O)_3$ | — | Allyl | 69–70 |
| 10 | $C_{13}$-$C_{15}$—alkyl (oxo) | $(C_2H_4O)_5$ | $(C_3H_8O)_2$ | — | $CH_3$ | 68 |
| 11 | $C_{13}$-$C_{15}$—alkyl (oxo) | $(C_2H_4O)_6$ | $(C_4H_8O)_2$ | — | $CH_3$ | 61 |
| 12 | octylphenol | $(C_2H_4O)_6$ | $(C_3H_6O)_4$ | — | $CH_3$ | 64–66 |
| 13 | $C_9$-$C_{11}$—alkyl (oxo) | $(C_2H_4O)_5$ | $(C_3H_6O)_3$ | — | $C_2H_5$ | 69–70 |
| 14 | $C_{13}$—alkyl (oxo) | $(C_2H_4O)_9$ | $(C_3H_6O)_2$ | — | n-$C_4H_9$ | 64–65 |
| 15 | $C_{22}$—alkyl | $(C_2H_4O)_8$ | $(C_3H_6O)_3$ | — | $CH_3$ | 62 |
| 16 | $C_8$—alkyl (oxo) | — | $(C_3H_6O)_3$ | $(C_2H_4O)_3$ | $CH_3$ | 68–70 |
| 17 | $C_9$-$C_{11}$—alkyl (oxo) | $(C_2H_4O)_5$ | — | — | Isopropyl | 70–72 |
| 18 | $C_{13}$-$C_{15}$—alkyl (oxo) | $(C_2H_4O)_9$ | $(C_4H_8O)_2$ | — | Benzyl | 64–65 |

*Butylene diglycol

EXAMPLES OF USE

The efficiency of antifoams in solutions as occur in the sugar industry and yeast industry can be tested in the laboratory as described below.

In a continuous circulation apparatus having a calibrated tube of 6 cm diameter, a test jet under constant pressure flows into a stock solution which contains a foam generator. During the procedure, a specific foam height is achieved, this height being measured in ml and being a measure of the foam formation. If, in addition to the foam generator, an antifoam is added to the test solution, the effect of the antifoam can be determined. The foam generator used is an alkylglucoside or a commercial saponin mixed with a $C_{13}/C_{15}$-oxoalcohol ether sulfate. The tests were carried out at from 70° to 75° C., depending on the temperature in the diffusors, in the clarification apparatuses or in the evaporators.

The results are summarized in Tables 2 and 3 below. Foam was produced using a solution of 0.4 g/l of decyl glucoside, and the foam volume was measured after from 1 to 5 minutes, as a function of the various antifoams.

TABLE 2

| Antifoam | Amount (ppm) | Foam volume (ml) | | | | |
|---|---|---|---|---|---|---|
| | | 1 | 2 | 3 | 4 | 5 min |
| without antifoam | — | 17 | 26 | 32 | 37 | 37 |
| Example 1 | 15 | 6 | 11 | 13 | 14 | 15 |
| Example 10 | 15 | 12 | 18 | 17 | 15 | 15 |
| Example 11 | 15 | 9 | 18 | 20 | 17 | 16 |
| Example 17 | 15 | 12 | 15 | 15 | 15 | 15 |
| Example 2 | 15 | 6 | 10 | 12 | 14 | 15 |
| Example 4 | 15 | 5 | 10 | 12 | 13 | 14 |
| Example 9 | 15 | 8 | 13 | 15 | 16 | 17 |
| Example 8 | 15 | 9 | 12 | 14 | 16 | 18 |

TABLE 3

Comparative examples without blocked terminal groups (formula I, Z = H)

| Antifoam | Amount (ppm) | Foam volume (ml) | | | | |
|---|---|---|---|---|---|---|
| | | 1 | 2 | 3 | 4 | 5 min |
| According to Example 1 Z = H | 15 | 15 | 21 | 23 | 25 | 25 |
| | 30 | 8 | 11 | 13 | 15 | 15 |
| According to Example 10 Z = H | 15 | 14 | 20 | 22 | 23 | 25 |
| According to Example 11 Z = H | 15 | 13 | 20 | 22 | 25 | 26 |
| | 30 | 8 | 17 | 19 | 20 | 21 |
| According to Example 17 Z = H | 15 | 18 | 25 | 33 | 36 | 36 |

The results show that etherification results in a reinforcement of the foam-inhibiting action in a manner which is not obvious. As a rule, it is necessary to use twice the amount, ie. 30 ppm, of a compound in which the terminal groups are not blocked, in order to achieve roughly similar inhibition of foam.

Similar results are obtained if, instead of decyl glucoside, saponin MT, together with a $C_{13}$-$C_{15}$-oxoalcohol ether sulfate, is used as a foam producer. As shown in Table 2, changing from a compound of the formula I where Z is H to a compound of the formula I where Z is methyl, ethyl, propyl, etc. results in a doubling of the foam-inhibiting potential in many cases, even under these altered conditions.

The products according to the invention not only possess an excellent foam-inhibiting action in the high-temperature processes in the sugar industry and yeast industry but, because of their turbidity points coupled with their excellent dispersibility, can also be used with similar success in the washing of beet at 20° C. or for inhibiting foam in fermentation vats. Here too, the small amount used is a great advantage.

In addition to being used as individual compounds, the antifoams according to the invention may also be employed in combination with conventional natural products, such as glycerol monooleate, wool fat, liquid paraffin, castor oil or fatty alcohols, or for reinforcing commercial antifoams which in turn are composed of, for example, soap, fatty alcohols and hydrocarbons, peanut oil, glycerol monooleate and mineral oil, or fatty acid oxyethylate light ends and glycerol monooleate.

In the yeast industry, too, the novel products can be used to control the foam profile in fermentation vats in a selective manner. The fact that the amounts used are smaller compared with the products used to date is noteworthy and hence advantageous.

We claim:

1. A process for controlling foam in the sugar industry and the yeast industry, wherein an oxyalkylation product of the formula I $$R-O-(X_1)_n-(X_2)_m-(X_3)_p-Z$$

where R is alkyl of 6 to 22 carbon atoms or alkylphenyl where alkyl is of 6 to 12 carbon atoms, $X_1$ and $X_3$ are each ethylene oxide units, n and p are each from 0 to 15 and the sum of n and p is not less than 2, the groups $X_2$ are propylene oxide and/or butylene oxide units, m is from 0 to 15 and Z is straight-chain or branched alkyl of 1 to 4 carbon atoms, allyl or benzyl, having a turbidity point of <75° C., is used as an antifoam.

2. A process as claimed in claim 1, wherein an oxyalkylation product of the formula I, where R is alkyl of 8 to 18 carbon atoms, is used.

3. A process as claimed in claim 1, wherein an oxyalkylation product of the formula I, where n+p is from 2 to 10 and m is from 2 to 12, is used.

4. A process as claimed in claim 1, wherein an oxyalkylation product of the formula I, in which the molar ratio of ethylene oxide to propylene oxide is from 3:1 to 1:3, is used.

5. A process as claimed in claim 1, wherein an oxyalkylation product of the formula I, which possesses blocked terminal groups and in which R is a $C_9$-$C_{11}$-alkyl radical obtained by the oxosynthesis, a $C_{13}$-$C_{15}$-alkyl radical obtained by the oxosynthesis or a $C_{10}$-$C_{14}$-alkyl radical obtained by the Ziegler synthesis, is used.

6. A process as claimed in claim 1, wherein an oxyalkylation product possessing blocked terminal groups is used together with other conventional antifoams.

7. A process as claimed in claim 1, wherein an oxyalkylation product of the formula I, where R is alkyl of 8 to 18 carbon atoms, n+p is from 2 to 10, m is from 2 to 12, and the molar ratio of ethylene oxide to propylene oxide is from 3:1 to 1:3, is used.

* * * * *